United States Patent [19]

Ezure et al.

[11] Patent Number: 4,806,633
[45] Date of Patent: Feb. 21, 1989

[54] METHOD OF MANUFACTURING MORANOLINE DERIVATIVES

[75] Inventors: Yoji Ezure, Otsu; Masashi Yamamoto, Kyoto; Shigeaki Maruo, Ibaraki; Makoto Sugiyama, Kyoto, all of Japan

[73] Assignee: Nippon Shinyaku Co., Ltd., Kyoto, Japan

[21] Appl. No.: 39,012

[22] Filed: Apr. 15, 1987

[30] Foreign Application Priority Data

Apr. 15, 1986 [JP] Japan ................................. 61-087509

[51] Int. Cl.$^4$ ...................... C07H 17/02; C07H 5/06; C08B 37/16; A61K 31/73
[52] U.S. Cl. .................... 536/18.5; 536/17.4; 536/18.6; 536/124; 536/127; 514/866
[58] Field of Search ............... 536/17.4, 17.9, 18.5, 536/18.6, 124, 127; 514/866

[56] References Cited

U.S. PATENT DOCUMENTS

| | | | |
|---|---|---|---|
| 4,235,888 | 11/1980 | Stadler et al. | 536/13.9 |
| 4,338,433 | 7/1982 | Matsumura et al. | 514/866 |
| 4,363,802 | 12/1982 | Matsumura et al. | 536/17.4 |
| 4,526,784 | 7/1985 | Heiker et al. | 536/18.5 |
| 4,634,765 | 1/1987 | Liu | 536/17.9 |

FOREIGN PATENT DOCUMENTS

| | | | |
|---|---|---|---|
| 0186103 | 7/1986 | European Pat. Off. | 514/866 |
| 2067989 | 8/1981 | United Kingdom | 514/866 |
| 2067990 | 8/1981 | United Kingdom | 514/866 |

OTHER PUBLICATIONS

Y. Ezure, Agric. Biol. Chem., 49 (7), pp. 2159–2165 (1985).
Kawamata, et al; Chemical Abstracts vol. 106:84991s Jun. 2, 1986.

*Primary Examiner*—Ronald W. Griffin
*Assistant Examiner*—Nancy S. Carson
*Attorney, Agent, or Firm*—Jacobs & Jacobs

[57] ABSTRACT

A method of preparing a molecular compound of glucosylmoranoline of the formula I

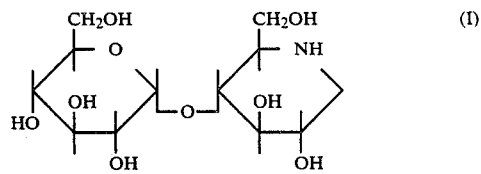

with methanol, which comprises stirring an aqueous solution comprising (I) and other moranoline derivatives with methanol, whereupon crystals of the molecular compound of (I) with methanol are formed.

5 Claims, No Drawings

METHOD OF MANUFACTURING MORANOLINE DERIVATIVES

The present invention relates to a method of making a glucosylmoranoline derivative of formula (I):

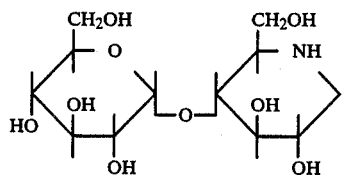

Compound (I) has a marked inhibitory action against blood sugar increase when administered to a sugar-loaded animal, and hence is useful as a therapeutic agent for the treatment of diabetes mellitus. (cf. Japanese Laid Open Application No. 56/081595).

The prior art discloses a method of making compound (I) in which an aqueous solution containing moranoline of the formula (III)

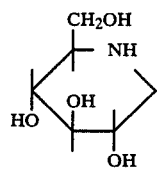

and cyclodextrin or soluble starch is contacted with cyclodextrin glycosyltransferase (EC 2.4.1.19) to produce a mixture of compound (I) and oligoglucosylmoranoline derivatives represented by the formula (II)

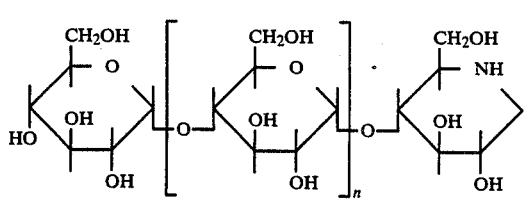

(wherein n is an integer of 1 to 5). The reaction solution contains unreacted (III) and by product (II) in addition to the desired compound (I), the ratio of these compounds varying depending upon the reaction conditions. Accordingly, the reaction mixture had to be worked up to isolate compound (I), which then had to be purified.

In accordance with another proposal, compound (II) can be converted to compound (I) in high yield by treating the above reaction mixture with glucoamylase (alpha-1,4-glucanglucohydrolase EC 3.2.1.3) (cf. Japanese Laid Open Application No. 57/058890). Although this is a good method of manufacturing, unreacted (III) is still present in the mixture after the treatment with glucoamylase and, in addition, 4-O-alpha-D-maltosylmoranoline and a very small amount of (II) are also obtained under certain reaction conditions.

To recover the desired compound (I) from such a reaction solution, it was necessary to employ molecular weight fractionation using Sephadex or the like or a reversed phase system column chromatography using Lichroprep CN (registered trademark; Merck Co) or Microbondapack-NH2. In order to overcome the above disadvantages, we have previously proposed the use of fractional crystallization with a polar solvent. See our Japanese Patent Application No. 59/237326 published June 2, 1986.

The present invention now provides an improved method of making compound (I) in higher yield, in higher purity, and without difficulty.

In particular, the present invention provides a method of preparing a molecular compound (as hereinafter defined) of methanol with glucosylmoranoline represented by the formula (I)

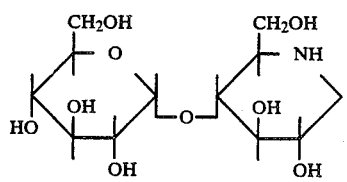

wherein an aqueous solution of glucosylmoranoline (I), oligoglucosylmoranoline represented by the formula (II)

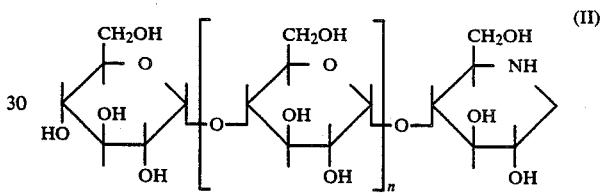

(wherein n is an integer of 1 to 5), and moranoline represented by formula (III)

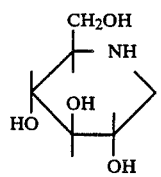

is admixed with methanol to form crystals of the molecular compound of methanol and (I).

The present invention also provides a method of preparing glucosylmoranoline represented by the formula (I)

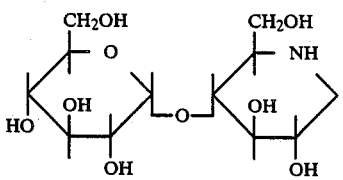

wherein an aqueous solution of a molecular compound of glucosylmoranoline (I) with methanol is admixed with ethanol to form crystals of glucosylmoranoline (I).

A primary feature of the present invention is that a mixture of the above (I), (II) and (III) is subjected to a so-called fractional crystallization using methanol, which is a polar solvent. Another feature of the present invention is that the mixture of (I), (II) and (III) is stirred during the fractional crystallization. The physico-chemical fact that such a very simple operation as stirring results in a dramatically improved result is quite remarkable.

In conducting the present invention, cyclodextrin glycosyltransferase is contacted, for example, with an aqueous solution containing (III) and cyclodextrin or soluble starch to produce a mixture of (I) and (II), which is then treated with glucoamylase to convert (II) to (I). The reaction solution generally contains about 30% of unreacted (III) as well as a small amount of 4-O-alpha-D-maltosylmoranoline and a very small amount of other (II). In general, the total amount of (II) is not more than 2% of the whole.

In the method of the present invention, the above mixture is dissolved in water, with heating if desired, and methanol is added thereto. Then the solution is stirred, whereupon crystals are crystallized out. Good results may be obtained by stirring for about 10 to 50 hours, preferably 24 hours, and at about 100 to about 300 rpm, 200 rpm preferably. Of course, the stirring speed may be faster or slower and for more or less time. See, e.g. Table 1 hereinafter. Crystallized-out crystals are collected, for example, by filtration. The crystals may be recrystallized, if necessary, and may be dried, e.g. in vacuo.

The recovered crystals are crystals of a molecular compound of (I) with methanol. The term "molecular compound" of glucosylmoranoline (I) with methanol as used herein means that methanol combines with glucosylmoranoline (I) such that they are not so easily separated to thus form an adduct of glucosylmoranoline with methanol in which (I) is solvated with methanol.

Another feature with the present invention is to use fractional crystallization with ethanol of the molecular compound of (I) with methanol to purify the crystals.

Fractionation utilizing the difference in solubilities of a molecular compound of (I) with methanol in the separation of (I) from a mixture of (I), (II), and (III) gives good results but it will not be industrially useful unless (I) can be obtained in a pure state from the molecular compound of (I) with methanol. Removal of methanol from a molecular compound of (I) with methanol is quite difficult. For example, drying the molecular compound at 60° C. for 24 hours or more in vacuo is ineffective, while recrystallization from water gives only about 35% recovery and is not very practical from an industrial viewpoint. Accordingly it was previously necessary to dissolve the molecular compound in water, and to remove methanol by treatment with a strongly acidic ion exchange resin followed by thorough washing with water. The resin was then eluted with ammonia water, and the ammonia water evaporated in vacuo to provide crystals. This method is very troublesome and would unduly limit the effect of the present invention of obtaining (I) from a molecular compound of (I) with methanol.

In carrying out the present invention, purified (I) is obtained by dissolving the reaction product containing a molecular compound of (I) with methanol in water, if desired with heating, and then ethanol is added thereto. Then the solution is stirred, if necessary, whereupon crystals are crystallized out. Good results may be achieved by stirring for about 10 to about 50 hours, preferably about 24 hours, at a speed of about 100 to about 300 rpm, preferably about 200 rpm. However, the time and speed of stirring may be more or less than stated. The crystals separated out can be collected, for example, by filtration. The crystals may be recrystallized, if necessary. Further, the crystals may be dried in vacuo or other means may be used to dry the crystals. According to tests conducted by the present inventors, the crystals thus obtained contain only 0.03 to 0.1% of ethanol as a residual solvent. Ethanol does not form a molecular compound with (I) and, in addition, is in a small amount in the purified crystals of (I) that is acceptable in the pharmaceutical industry. Since the methanol content of the crystals is not more than 50 ppm, it can be seen that methanol can be entirely removed from the molecular compound of (I) with methanol in an industrially acceptable sense.

It has been known that, in general, a molecular compound having a solvent as a component is not easily soluble in that solvent. The solubilities of (III) and (I) in aqueous methanol are nearly the same and it has been confirmed by the present inventors that, as time goes on, the solubility of (I) decreases. It is believed that this is due to the fact that (I) forms a molecular compound with methanol as time proceeds, whereupon the solubility thereof decreases.

It has also been known that, in general, even when the solubilities in solvents are the same, there is a difference among substances as to the time during which they are stable under supersaturated conditions, this time being called the crystallization-initiating time. Generally, such a time for sugars in aqueous solvents is long. However, the present invention includes the discovery that the crystallization-initiating time is shortened by a simple stirring operation. The relationship between the stirring and the shortening of the crystallization-initiating time could not have been predicted.

In the present invention, ethanol is used in the fractional crystallization operation but the reason why ethanol expels methanol from the molecular compound and why compound (I) does not form a molecular compound with ethanol while it does with methanol is not fully understood and could not have been predicted.

In accordance with the present invention, it is possible to manufacture the desired compound (I) of high purity by a simple method, whereas the prior art used carbon column chromatography or column chromatography with alkali metal or alkali earth metal type strongly acidic cation exchange resin, which are very complicated processes.

The present invention is also advantageous because the crystallization-initiating time is reduced. It has been previously necessary to allow the reaction mixture to stand for a very long time to increase the purity and yield of the desired compound whereas in the present invention, a practical time can be used, whereby the present invention is industrially advantageous.

The present invention method is also useful in the pharmaceutical industry, because methanol, which is harmful to the human body can be removed from the molecular compound of methanol and (I).

The present invention is further illustrated by the following Reference Examples and Examples.

TEST EXAMPLE 210 mg of glucosylmoranoline (GM) and 90 mg of moranoline (M) were placed in 50 ml flasks and were dissolved in 0.3 ml of water at 60° C. Methanol (8.7 ml) was added to each flask, and the flasks were kept at 5° C. or at 20° C. One flask of each set was allowed to stand and the other was stirred at 200 rpm using a magnetic stirrer. The solution was taken out therefrom periodically, centrifuged, and the supernatant liquid was analyzed by a high performance liquid chromatography. The analytical conditions were the same as those in the Reference Example 1 hereinafter. The results are shown in Table 1, which report the amounts of GM and M that dissolved with respect to time.

TABLE 1

| Time Elapsed (hours) | Substance | Amount Dissolved (g/liter) | | | |
|---|---|---|---|---|---|
| | | 5° C. | | 20° C. | |
| | | stirred | stand | stirred | stand |
| 0 | M | 10.0 | 10.0 | 10.0 | 10.0 |
| | GM | 23.0 | 23.0 | 23.0 | 23.0 |
| 1.5 | M | 10.2 | 9.8 | 10.5 | 9.7 |
| | GM | 5.5 | 22.1 | 6.2 | 21.1 |
| 3.0 | M | 10.1 | 10.1 | 11.4 | 9.9 |
| | GM | 4.2 | 22.0 | 4.4 | 21.3 |
| 10.0 | M | 9.9 | 10.0 | 10.2 | 9.8 |
| | GM | 3.1 | 19.0 | 3.2 | 18.2 |
| 24.0 | M | 6.8 | 10.1 | 10.5 | 9.7 |
| | GM | 3.2 | 9.7 | 3.1 | 7.9 |

In the table, the term "stand" means that the flask was shaken by hand for 4 to 5 times a day to mix the contents.

It will be apparent from Table 1 that in the case of moranoline there was nearly no change in the solubility until 10 hours both in "stirred" and "stand" conditions. When stirred, there was a tendency that, at 5° C. for 24 hours, the solubility decreases.

On the contrary, in the case of glucosylmoranoline, there was nearly no change until 3 hours both at 5° C. and 20° C. in the "stand" conditions, whereas at 10 hours there was a decrease in solubility and then the amount dissolved was one half of the initial amount after 24 hours. In the samples of GM that were stirred, the amount dissolved decreased to one quarter after only 1.5 hours. Table 1 shows that the effect of the stirring on the dissolved amount of GM is quite large, and there is little effect of temperature on the solubility of GM.

REFERENCE EXAMPLE 1

(1) Moranoline (21 g) was dissolved in a small amount of water and the solution was adjusted to pH 5.7 with 6N hydrochloric acid. After the adjustment, water was added to make 350 ml. Soluble starch (72 g) was dissolved therein while the solution was still hot. After that, the solution was kept at 50° C., 350 ml of crude enzyme solution of 1000 units/ml of cyclodextrin glycosyltransferase was added, and the mixture was allowed to react at 50° C. for two days. After the reaction, the mixture was heated at 80° C. for 15 minutes, 5.6 g of glucoamylase (Glucozyme AF-6 manufactured by Amano Seiyaku KK) was added, and the mixture was allowed to react at 50° C. for 24 hours. After the reaction, the product was heated at 80° C. for 15 minutes, centrifuged and the supernatant fluid was passed through a column of Dowex 50W×2 (H+) (wherein the amount of the resin was 500 ml), and the basic substance was absorbed therewith. The column was thoroughly washed with water, eluted with 1N ammonia water, the eluate was concentrated in vacuo, and the concentrated solution was passed through a column of a strongly basic ion exchange resin (Diaion SA-11A, the amount of the resin=100 ml). This was thoroughly washed with water and both the solution passed through the resin and the washings were combined, followed by concentration in vacuo to dryness whereupon 34.8 g of powder was obtained.

This was analyzed by high performance liquid chromatography and was found to be a mixture comprising 26.1% of moranoline, 71.9% of glucosylmoranoline and 2% of 4-O-(alpha-D-maltosyl)-moranoline.

The conditions used for the high performance liquid chromatography were as follows:

Sumipax R741 (Nucleosil 5NH$_2$, 5 micrometers, 4 mm ID×25 cm). Developer: acetonitrile-water (70:30); Flowing rate: 1 ml/min; RI Detection (ERC-7510 manufactured by Elmer Kogyo KK); Data processor: Type 655-60 manufactured by Hitachi Ltd.

REFERENCE EXAMPLE 2

Moranoline (21 g) was subjected to the same reaction as in Reference Example 1 with the exception that 7 g of glucoamylase was used and the reaction was carried out at 50° C. for 24 hours.

The reaction product was treated as same in Reference Example 1 to give 31 g of powder.

This was analyzed by the same manner as in Reference Example 1 by a high performance liquid chromatography and was found to be a mixture comprising 29.2% moranoline, 70.0% glucosylmoranoline and 0.8% 4-O-(alpha-D-maltosyl)-moranoline.

EXAMPLE 1

The mixture (34.7 g) of moranoline, glucosylmoranoline and 4-O-(alpha-D-maltosyl)-moranoline obtained from Reference Example 1 was dissolved in 83 ml of water, a magnetic stirrer was placed therein, and 1305 ml of methanol was added with stirring at about 200 rpm. This was stirred at room temperature overnight and the crystals that had separated out were collected by filtration followed by drying in vacuo at 60° C. for 16 hours to give 22.4 g of crystals. The resulting crystals contained 6.8% (w/w) of methanol and, upon analysis by a high performance liquid chromatography, its purity as glucosylmoranoline was 99.9% Rate of recovery was 83.3%.

$[\alpha]_D^{24} + 114.3°$ (c, 1.07% water).

Elementary Analysis calculated for $C_{12}H_{23}NO_9.0.65CH_3OH$: Calcd (%): C 43.90, H 7.45, N 4.05; Found (%): C 43.65, H 7.76, N 4.15

$^1$H-NMR: δ (ppm); 2.45 (1H, dd, J1a, 1e, 12.3 Hz, J1a, 2, 10.3 Hz, H1a), 2.61~2.72 (1H, m, H5), 3.11 (1H, dd, J1a, 1e 12.3 Hz, J1e, 2, 4.9 Hz, H1e), 3.34 (2.4H, s, CH$_3$OH), 3.35~3.88 [11H, m, 4H (—CH$_2$OH), 5H (—CH-OH), 1H (H-4), 1H (H-5')], 5.32 (1H, d, 3.7 Hz, H-1', Anomeric Proton)

The crystals were dried in vacuo at 60° C. and the amount of the residual methanol was measured. When dried for 10 hours, it was 7.5% in both pulverized and nonpulverized crystals; after 16 hours, it was 6.6 and 6.8%, respectively; and after 10 hours more, it was 6.3 and 6.9%, respectively. From those results, it is apparent that the methanol was quite strongly incorporated in the glucosylmoranoline, which corroborates that a molecular compound with methanol was formed.

Measurement of the residual methanol was conducted by gas chromatogrpahy as per the following conditions.

Apparatus: Gas-Chro Model 103C (manufactured by Okura Rikagaku KK); Column: G-0, 1 m; Temperature: Injection 200° C., column 120° C.; Carrier: 1.0 kg/cm$^2$ nitrogen calculated as water (10 microliters/minute).

EXAMPLE 2

The crystals (10 g) obtained in Example 1 were dissolved in 20 ml of water at 60° C., the solution was cooled by allowing it to stand until ambient temperature was reached, and 90 ml of ethanol was added thereto with stirring with a magnetic stirrer. This was stirred overnight. The crystals that separated out were collected by filtration and dried at 60° C. for 16 hours in vacuo 7.5 g of crystals were obtained. Rate of recovery=80.5%.

The residual solvent therein was measured by gas chromatography in the same manner as in Example 1 and about 0.06% of ethanol was found. The methanol content was not more than 0.005% and the purity of the glucosylmoranoline was 100%.

EXAMPLE 3

The mixture (10 g) obtained by Reference Example 2 was dissolved in 15 ml of water and 285 ml of methanol was added with stirring using a magnetic stirrer. This was stirred overnight and the crystals that separated out were collected by filtration. They were dried in vacuo at 60° C. for 10 hours to give 7.1 g of crystals. Rate of recovery=91.7%.

This was analyzed by high performance liquid chromatography and found to contain 3.1% of moranoline and 96.9% of glucosylmoranoline. Also detected was 6.1% of residual methanol.

EXAMPLE 4

The crystals (7 g) obtained in Example 3 were dissolved in 14 ml of water at 60° C., the solution was allowed to cool to ambient temperature, and 66 ml of ethanol was added with stirring at ambient temperature. This was stirred overnight, the crystals separated out therefrom were collected, dried at 60° C., for 16 hours in vacuo. 5.3 g of crystals were obtained. Rate of recovery=81.5%.

The residual solvent of that product was measured and found to be 0.05% of ethanol and not more than 0.005% of methanol. Purity as glucosylmoranoline was 100%.

The Examples illustrate presently preferred conditions of operation. In general, a wide range of proportions of methanol to the mixture of (I), (II) and (III) may be used. Likewise, a wide range of proportions of ethanol to the solution of the molecular compound of (I) with methanol and/or crystals of the molecular compound may be used. For example, the amount of methanol per gram of the solution comprising (I), (II) and (III) may be from about 1 to about 1000 ml, most preferably from about 5 to about 100 ml. Further, the amount of ethanol per gram of the solution comprising the crystals of the molecular compound or the crystals themselves may be from about 1 to about 1000 ml, preferably from about 1 to about 250 ml, most preferably from about 1 to about 50 ml.

We claim:

1. A method of preparing a molecular compound of glucosylmoranoline represented by the formula (I)

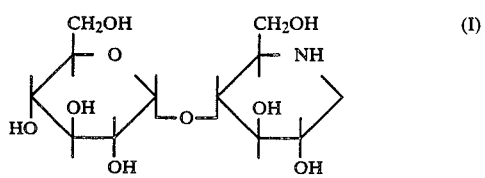

with methanol, which comprises admixing an aqueous solution of glucosylmoranoline (I), oligoglucosylmoranoline represented by the formula (II)

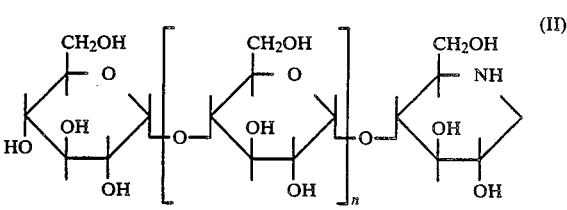

(wherein n is an integer of 1 to 5), and moranoline represented by formula (III)

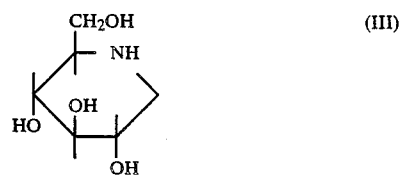

with methanol and stirring the admixture to form crystals of the molecular compound of methanol and (I).

2. The method according to claim 1, wherein said admixture is stirred for about 1.5 to about 50 hours at about 1000 to about 300 rpm.

3. The method according to claim 2, wherein said admixture is stirred about 24 hours at about 200 rpm.

4. The method according to claim 1, wherein said crystals of said molecular compound of (I) and methanol are recovered and dried.

5. A method of preparing glucosylmoranoline represented by the formula (I)

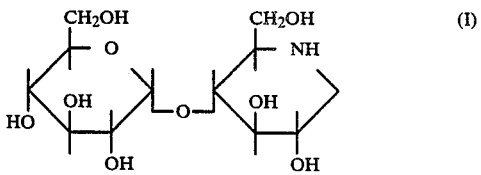

which comprises admixing an aqueous solution of a molecular compound of glucosylmoranoline (I) and methanol with ethanol to form crystals of glucosylmoranoline (I).

* * * * *

UNITED STATES PATENT AND TRADEMARK OFFICE
CERTIFICATE OF CORRECTION

PATENT NO. : 4,806,633
DATED : February 21, 1989
INVENTOR(S) : YOJI EZURE; MASASHI YAMAMOTO; SHIGEAKI MARUO; and MAKOTO SUGIYAMA It is certified that error appears in the above-identified patent and that said Letters Patent is hereby corrected as shown below:

Claim 2, line 3, change "1000" to -- 100 --.

Signed and Sealed this

Tenth Day of September, 1991

Attest:

HARRY F. MANBECK, JR.

Attesting Officer

Commissioner of Patents and Trademarks